(12) United States Patent
Blake, III

(10) Patent No.: US 8,486,098 B2
(45) Date of Patent: Jul. 16, 2013

(54) AORTIC PUNCH

(76) Inventor: Joseph W Blake, III, New Canaan, CT (US)

( * ) Notice: Subject to any disclaimer, the term of this patent is extended or adjusted under 35 U.S.C. 154(b) by 1515 days.

(21) Appl. No.: 11/705,360

(22) Filed: Feb. 12, 2007

(65) Prior Publication Data

US 2009/0138033 A1 May 28, 2009

(51) Int. Cl.
*A61B 17/14* (2006.01)

(52) U.S. Cl.
USPC .......................................... 606/184

(58) Field of Classification Search
USPC .................. 606/159, 167, 170, 184
See application file for complete search history.

(56) References Cited

U.S. PATENT DOCUMENTS

| | | | | |
|---|---|---|---|---|
| 4,018,228 | A | * | 4/1977 | Goosen ........................ 606/184 |
| 4,216,776 | A | * | 8/1980 | Downie et al. ................ 606/184 |
| 5,129,913 | A | * | 7/1992 | Ruppert ....................... 606/184 |
| 5,192,294 | A | * | 3/1993 | Blake, III ...................... 606/184 |
| 5,827,316 | A | * | 10/1998 | Young et al. .................. 606/185 |
| 5,910,153 | A | * | 6/1999 | Mayenberger ............... 606/184 |
| 6,022,367 | A | * | 2/2000 | Sherts .......................... 606/184 |
| 6,036,710 | A | * | 3/2000 | McGarry et al. .............. 606/184 |
| 6,080,173 | A | * | 6/2000 | Williamson et al. .......... 606/184 |
| 6,428,555 | B1 | * | 8/2002 | Koster, Jr. .................... 606/185 |
| 6,673,088 | B1 | * | 1/2004 | Vargas et al. ................. 606/185 |
| 2002/0082614 | A1 | * | 6/2002 | Logan et al. ................. 606/139 |
| 2003/0069595 | A1 | * | 4/2003 | Phung et al. ................. 606/184 |
| 2004/0049221 | A1 | * | 3/2004 | Loshakove et al. ........... 606/184 |
| 2004/0098011 | A1 | * | 5/2004 | Vargas et al. ................. 606/184 |

* cited by examiner

*Primary Examiner* — Ryan Severson
*Assistant Examiner* — Jonathan W Miles
(74) *Attorney, Agent, or Firm* — Patrick J. Walsh

(57) ABSTRACT

An aortic punch including a handle mechanism and punch cartridge for interchangeability of a variety of cartridges with a common handle.

7 Claims, 4 Drawing Sheets

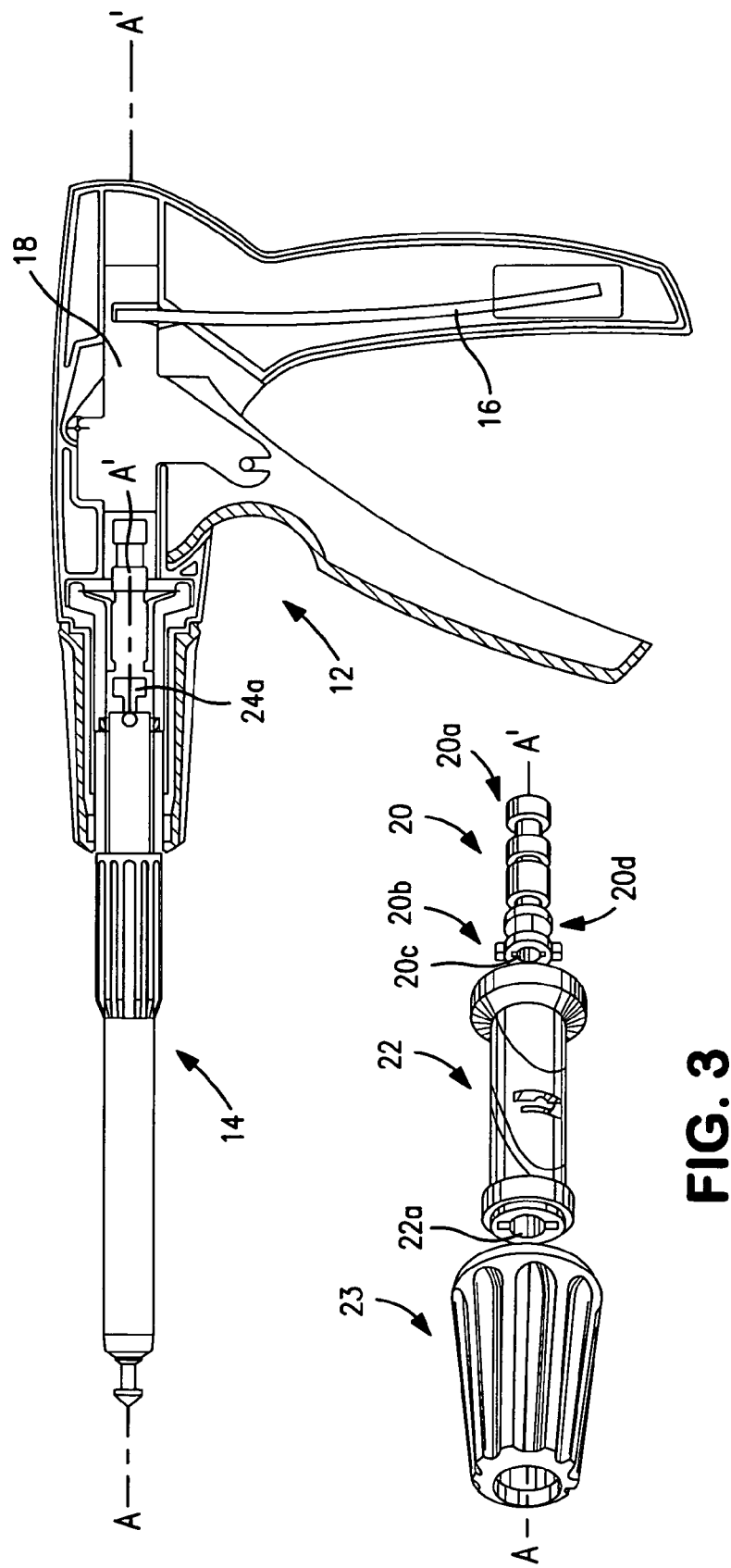

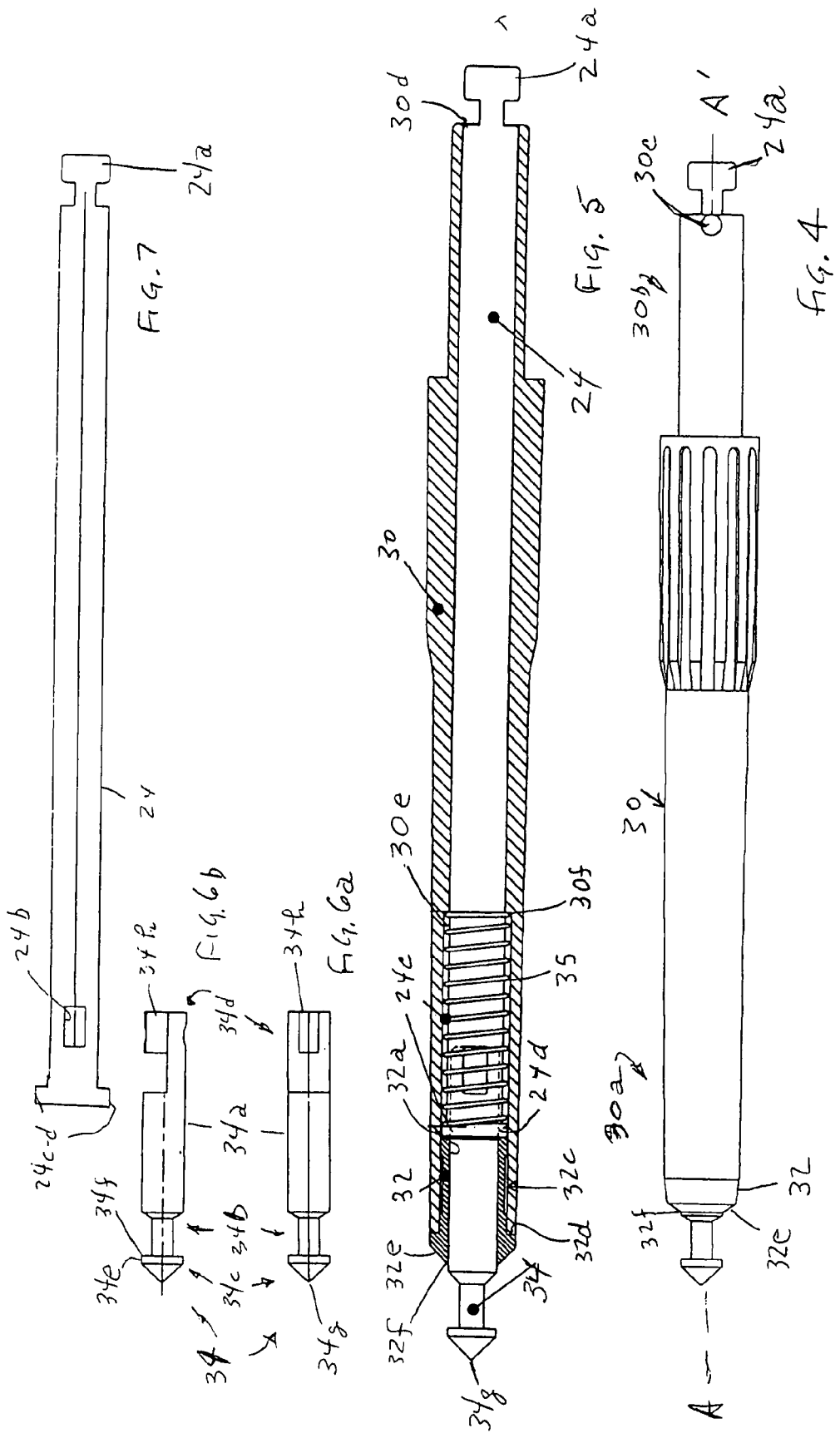

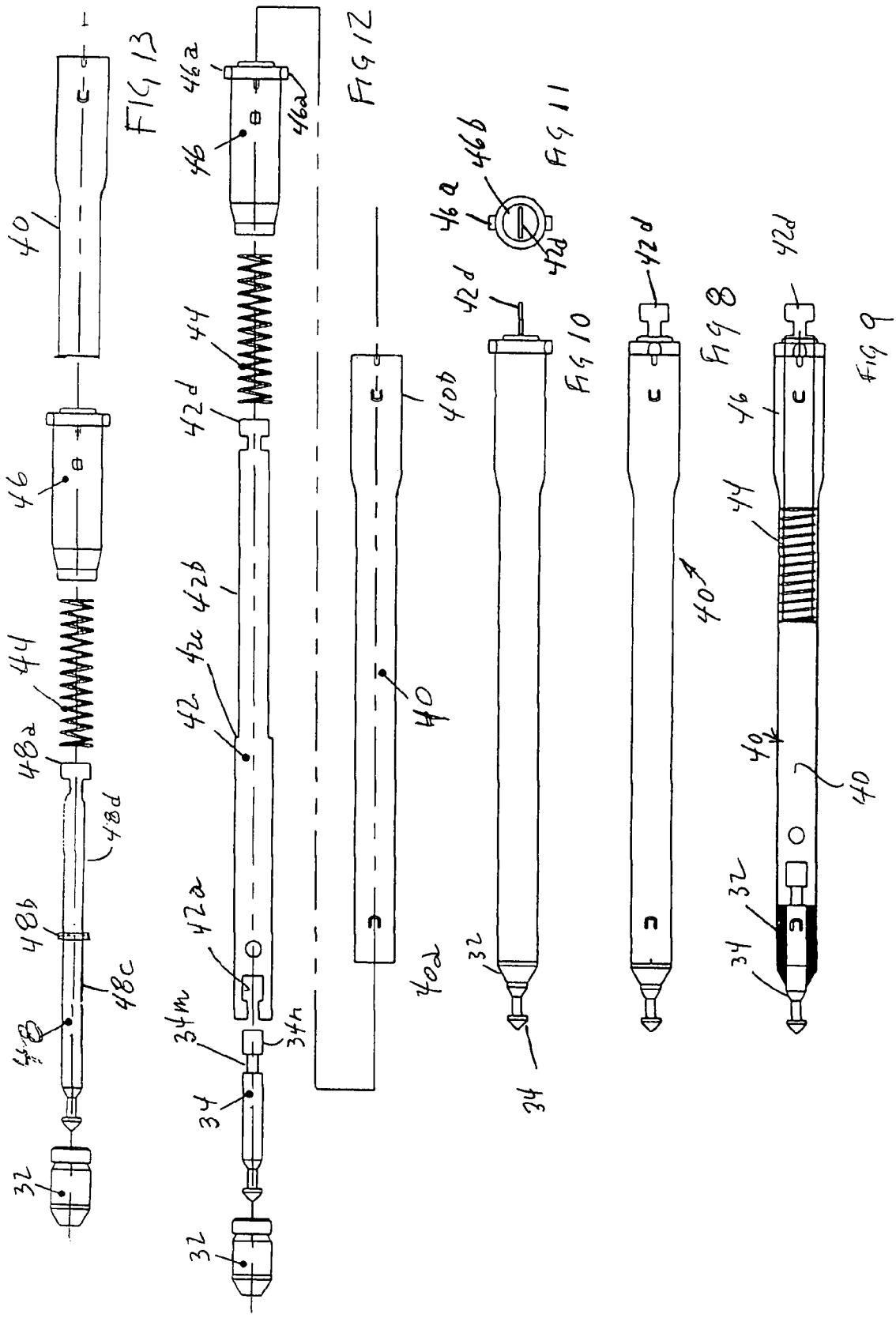

AORTIC PUNCH

FIELD OF THE INVENTION

The present invention relates to aortic punches for removing tissue from the vascular system in surgical procedures.

BACKGROUND OF THE INVENTION

In cardiac surgery blood vessel walls are opened by a vascular or aortic punch to provide an opening of suitable configuration for attachment of arteries or veins as required in carrying out a cardiac surgical procedure. Initially, a blood vessel wall is slit with a scalpel creating a small incision through the wall for insertion of a punch head. An aortic punch removes a small disc, of tissue from a blood vessel wall by withdrawing the punch head and surrounding tissue through a cutting die. The disc so removed is retained by the punch head while a corresponding hole remains in the blood vessel defining a suitable opening for attachment of vein or artery in continuing with a cardiac procedure.

A vascular punch of this kind is disclosed in my U.S. Pat. No. 5,192,294, which comprises a pistol-like housing for positioning and actuating a vascular punch in surgery. The '294 vascular punch is an integrated device in which tissue removal components and their actuating components are permanently assembled in the pistol-like housing for the duration of the useful life of the punch, whether reused or disposed of as title of the '294 patent suggests.

It is desirable in surgical practice that different configurations of aortic punch be available to meet the variable operating site conditions encountered in practice. With prior art devices such as the '294 patent, these desirable arrangements are meet only by keeping an inventory of integrated devices each with its own pistol grip and specific punch configuration. It is also desirable to meet the requirements of endoscopic surgery particularly constraints involved in using a trocar for passing instruments to a surgical site.

There is need for an arrangement in which a common pistol grip or other handle configuration is suitable for a variety of punch configurations selected to meet specific operating site constraints of cardiac surgery.

SUMMARY OF THE INVENTION

The present invention comprises an aortic punch comprising an operating handle and an aortic punch cartridge wherein a single handle accommodates a variety of punch cartridges individually configured according to operating site constraints. An operating handle providing linear reciprocating motion including scissors-type or pistol grip is used with the invention. A suitable operating handle is disclosed in my U.S. Pat. No. 6,869,435 entitled Repeating Multi-clip Applier. The '435 operating handle housing accommodates a pistol grip set of handles to provide linear reciprocating motion by means of a spring biased translator slide. The operating handle housing includes a rotary finger wheel hub and rotatable drum subassembly which connect to a surgical clip applying cartridge and which link the cartridge to the translator slide. The operating handle defines a unique interface between handle and cartridge thereby permitting variation in cartridge design to meet constraints encountered in surgical practice.

The present invention provides an aortic punch in the form of a cartridge suitable for use with a '435 operating handle.

The operating handle contains all components needed to impart linear reciprocating movement to an aortic punch cartridge including means for moving the punch components in a first linear direction, and for returning the punch to normal or starting position. Because of this arrangement, an aortic punch cartridge according to the invention is simplified to minimum components needed to achieve its function.

In conjunction with the operating handle, an anti back-up mechanism prevents return of the handle, if released by a surgeon in mid-stroke, until full handle stroke is completed. The punch thereby retains excised tissue for removal from surgery site.

An aortic punch cartridge according to the invention comprises a tubular outer housing, a blade drum defining a circular cutting edge fitted to an open of the housing, a punch mandrel fitted into the blade drum, and a connecting link between punch mandrel and operating handle. The dimensions and shape of the aortic punch cartridge are chosen as desired to meet constraints encountered during cardiac or vascular surgery.

The invention simplifies logistic requirements for aortic punches in cardiac surgery in providing punch cartridges in a variety of sizes and configurations for interface with a common handle.

OBJECTS OF THE INVENTION

An object of the invention is to provide a novel aortic punch with minimum complexity and with adaptability to a complete range of cardiac surgery procedures.

Another object of the invention is to provide an aortic punch using a replaceable punch cartridge.

Another object of the invention is to provide an aortic punch having an operating handle that contains operating components needed for linear reciprocating motion thereby simplifying punch cartridge components.

Another object of the invention is to provide an aortic punch cartridge that can be used with various operating handle configurations including pistol grip, scissor type, surgical robot, as well as any actuating means for providing linear excursion.

Other and further objects of the invention will become apparent with an understanding of the following detailed description of the invention or upon employment of the invention in practice.

BRIEF DESCRIPTION OF THE DRAWING

A preferred embodiment of the invention has been chosen for detailed description to enable those having ordinary skill in the art to which the invention appertains to readily understand how to construct and use the invention and is shown in the accompanying drawing in which:

FIG. 2 is a side elevation view of the aortic punch of FIG. 1 with the operating handle housing partially in section and with handle in release position.

FIG. 3 is a perspective view of the handle components aligned on A-A' axis comprising the handle side interface with punch cartridge.

FIG. 4 is a plan view of aortic punch cartridge according to the invention.

FIG. 5 is a plan section view of the aortic punch of FIG. 4.

FIG. 6a is plan view of a punch mandrel of the aortic punch of FIG. 5.

FIG. 6b is a side elevation of punch mandrel of FIG. 6a.

FIG. 7 is a plan view of connecting link or pull bar of the aortic punch of FIG. 5.

FIG. 8 is a plan view of a modified embodiment of aortic punch cartridge according to the invention.

FIG. 9 is a sectional plan view showing internal components of the aortic punch cartridge of FIG. 8.

FIG. 10 is a side elevation view of the aortic punch cartridge of FIG. 8.

FIG. 11 is an end view of the aortic punch cartridge of FIG. 10.

FIG. 12 is an exploded view showing layout of components of aortic punch cartridge of FIG. 8.

FIG. 13 is another modified embodiment of the invention in exploded view showing layout of components of aortic punch cartridge.

DETAILED DESCRIPTION OF THE PREFERRED EMBODIMENT

Figure 1:
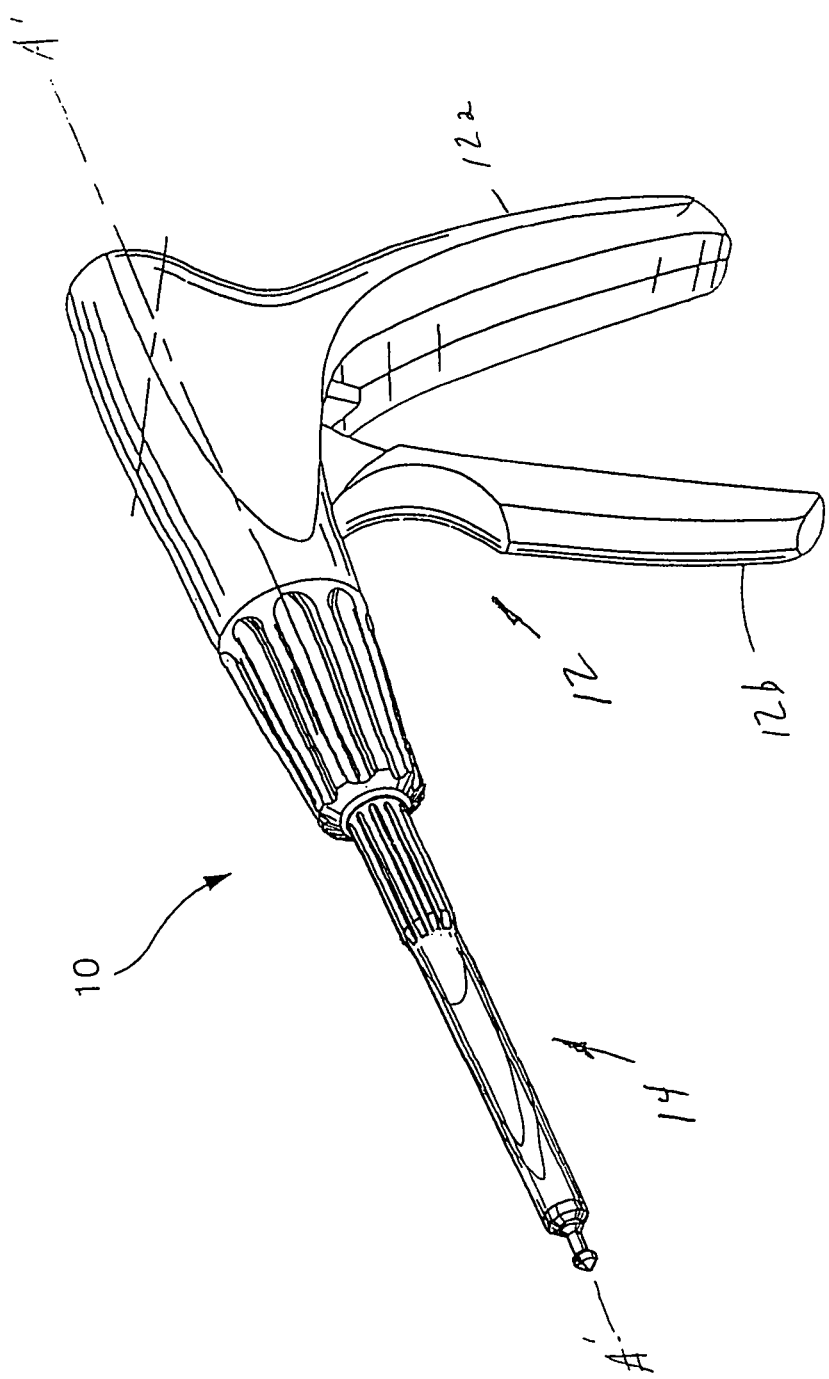
FIG. 1 is a perspective view of a preferred embodiment of aortic punch according to the invention, indicating it's A-A' axis.

Referring to the drawing, a preferred embodiment of aortic punch 10 comprises operating handle 12 and aortic punch cartridge 14.

The operating handle 12 shown in FIGS. 1 and 2 is fully described in my U.S. Pat. No. 6,869,435 and comprises a pistol grip 12a and trigger 12b that impart linear movement or linear excursion to internal components assembled within the housing. The internal components (FIG. 2) include bar spring 16, e.g., for biasing components forward within the housing, a linear translator 18 for true linear movement along the A-A' axis, a rotary translator 20, and a rotary drum 22 with finger wheel hub 23. The rotary translator is fitted at one end 20a to the linear translator and at its other end 20b defines an interface for receiving the punch cartridge 14.

As best shown in FIGS. 2 and 3, the rotary translator 20 is assembled within the rotary drum 22 with both the drum and translator having keyhole openings 22a, 20c through their front faces for passing an end of connecting link or pull bar 24 of the punch cartridge. The rotary translator is further provided with a front-end cage 20d for receiving connecting link end 24a, and for imparting linear movement to the link during operation of the aortic punch.

The rotary drum subassembly within the operating handle housing is now ready to receive the removable aortic punch cartridge, to impart both reciprocating rectilinear movement to the cartridge and to accommodate rotary movement of the cartridge. The rotary drum and rotary translator serve as a receptacle for the T-shaped end of a cartridge connecting link described below.

It is to be understood that the operating handle provides reciprocating liner motion of fixed length referred to herein as linear excursion. It is to be further understood that any suitable mechanism capable of providing reciprocating linear motion of fixed excursion including pistol grip and scissor type handles, surgical robot, as well as any actuating means for providing linear excursion may be used for operating the aortic punch cartridge.

The aortic punch cartridge (FIGS. 4-7) includes a housing 30 in the form of a tube along the A-A' axis with punch end 30a and handle end 30b. The punch end supports a blade drum or tissue cutting die 32 in the general form of a cylinder defining an interior passage 32a. The blade drum includes outer surface 32c terminating in a circumferential shoulder 32d for nesting engagement within the tube punch end 30c. The exposed end of the drum is conical 32e terminating in a circular cutting edge 32f against which a disc of tissue is cut from a vein or artery by a punch mandrel 34 during surgery.

The punch mandrel 34 occupies interior passage 32a of the blade drum. The punch mandrel 34 comprises a cylindrical shaft 34a with recess 34b at one end to form a punch head 34c. The punch mandrel is recessed at its other end 34d for assembly with connecting link 24. The punch head includes a cylindrical base 34e defining a circular cutting edge 34f cooperating with the blade drum cutting edge 32f for severing arterial tissue. The punch head has a conical tip 34g for ease of passage of the punch head through an entry incision formed in an artery wall.

The punch mandrel recess 34d has an integral block 34h for engagement with an aperture 24b in connecting link 24 for movement of the punch mandrel along the linear excursion of the handle.

The connecting link 24 is an elongate strip preferably of stamped sheet metal with T-shaped flange 24a for connection to a handle, aperture 24b for connection to punch mandrel block, and spring engaging shoulders 24c-d cooperating with cartridge spring 35 described below.

The aortic punch cartridge tube 30 at its handle end 30b has positioning pins 30c projecting radially from the tube, and an end slot 30d for passing the end of a connecting link or puller bar while maintaining radial alignment of the pins and puller bar. The connecting link or puller bar terminates in a T shape flange 24a for connection with the rotary translator forming part of the handle receptacle for the link.

The assembly of housing 30 and puller bar 24 is shown in FIG. 5 wherein the housing interior surface is recessed 30e to accommodate coil spring 35 encircling puller bar 24. Coil spring is placed between interior surface shoulder 30f and puller bar shoulders 24c-d so that rearward movement of the puller bar compresses the coil spring which returns the bar to the position shown in FIG. 5.

A modified form of aortic punch cartridge is shown in FIGS. 8-12. The modified punch includes a housing 40 in the form of a tube along the A-A' axis with punch end 40a and handle end 40b. The punch end supports a blade drum 32 and punch mandrel 34 which are the same as those in FIGS. 4-7 to the extent indicated by common reference numerals, and vary as indicated by added numerals.

The punch mandrel 34 is recessed by radial groove 34m to form a cyndrical connecting block 34n for assembly with connecting link 42 for movement of the punch mandrel along the linear excursion of the handle. Connecting link 42 comprises an elongate flat rod with forward slot 42a having a contour for coupling with punch mandrel block 34n, a necked-down portion 42b defined by shoulder 42c a terminal T-shaped flange 42d. A coil spring 44 occupies the necked-down portion of the connecting link engaging shoulder 42c to urge link and punch mandrel toward forward position.

The aortic punch cartridge housing tube at its handle end has a closure sleeve 46 that slides onto handle end of the housing. The sleeve has positioning pins 46a projecting radially, and an end slot 46b(FIG. 11) for passing the T-shape end of the connecting link while maintaining radial alignment of the pins and puller bar.

Another modified embodiment of aortic punch is shown in FIG. 13 in which components are the same as those in the embodiments of FIGS. 4-12 as indicated by common reference numerals. The aortic punch of FIG. 13 includes a punch mandrel 48 having a front end as described for FIGS. 4-12. Mandrel 48 is elongate and terminates in a T-shape flange 48a for direct connection of the mandrel to a handle mechanism. Fixed collar 48b defines a shoulder for engagement with coil spring 44 in an assembled punch. In preferred form, mandrel 48 is cylindrical for the portion 48c extending forward of shoulder 48b, and a flat strip 48d for that portion to the rear of the shoulder. This embodiment of aortic punch allows for a short-length aortic punch as is desirable in particular surgical procedures.

Referring to FIGS. 1-3 for assembly of aortic punch cartridge and operating handle:

(a) the aortic punch cartridge is inserted through keyhole into the front end of the rotary drum with cartridge positioning pins entering interior drum slots;

(b) the T flange projecting through cartridge end slot is in fixed radial orientation in relation to the positioning pins;

(c) the T flange approaches end face of the rotary translator with the T flange in axial registry with the keyhole in the front face of cage flange (FIG. 2);

(d) the T flange passes through the keyhole into the rotary translator cage;

(e) the cartridge is rotated (arrow 10a) on A-A' axis with cartridge pins entering radial drum slots and the T flange coming to rest against the rotary translator interior cage shoulders.

The slot spring engages one of the pins to hold the cartridge in assembled position with the handle.

The cartridge and operating handle are taken apart by reversing the assembly sequence.

It is to be understood that an aortic punch cartridge of this invention can be used with a scissor grip handle as well as with the pistol grip handle described above. For example, the scissor grip handle described in my. U.S. Pat. No. 6,423,079 modified to have a cartridge/handle interface as described above makes a suitable handle. It is within the purview of the invention for the cartridge to receive linear excursion from handles as described as well as from any mechanism whether manual or automatic capable of generating linear excursion and having a receptacle for interface with the cartridge puller bar T-flange.

Various changes may be made to the structure embodying the principles of the invention. The foregoing embodiments are set forth in an illustrative and not in a limiting sense. The scope of the invention is defined by the claims appended hereto.

I claim:

1. An aortic punch for removing tissue from a vascular system comprising a handle and a punch cartridge having a pull bar with an end connector, the handle having a linear translator for linear movement along an axis, a rotary drum, a rotary translator assembled within the rotary drum with both the drum and translator having openings for passing the pull bar end connector, the rotary translator fitted at one end to the linear translator and at its other end having a cage for receiving and retaining the end connector, the cartridge comprising a tubular housing having a longitudinal axis and having an open punch end and an open handle end, a blade drum positioned in the punch end of the housing, the blade drum having a closed cutting edge, the drum having an axial bore for slidably receiving a punch mandrel, the punch mandrel comprising a shaft with a circumferential recess for positioning vascular tissue in the aortic punch, the circumferential recess defining a punch head at an end of the shaft, the punch head having a closed cutting edge for cooperation with the drum cutting edge in removing vascular tissue, the punch mandrel having connecting means at the other end of the shaft, said pull bar secured to the mandrel connecting means and extending along the axis and through the handle end of the tubular housing, the pull bar end connector being engaged with the rotary translator of the handle mechanism so that linear excursion is imparted to the punch mandrel for removing vascular tissue at the blade drum, and the handle and cartridge being readily detachable to facilitate use in a surgical procedure of a single handle with a cartridge selected from a variety of cartridge sizes and configurations.

2. An aortic punch as defined in claim 1 in which the handle end of the cartridge housing has radial positioning pins, and further has an end slot for passing the pull bar end connector so as to maintain relative position of pins and pull bar for assembly of cartridge into handle, and for entry of end connector into rotary translator cage.

3. An aortic punch as defined in claim 1 in which the handle has an anti-backup mechanism.

4. An aortic punch as defined in claim 1 in which the punch mandrel connecting means comprises a cylindrical block, and in which the pull bar has a forward slot with a contour for coupling with the cylindrical block.

5. An aortic punch as defined in claim 1 in which the pull bar has a necked down portion defining a shoulder and in which a coil spring occupies the necked down portion and engages the shoulder to urge pull bar and mandrel to forward position.

6. An aortic punch as defined in claim 1 in which the cartridge housing wall has an interior recess defining a shoulder, a cartridge spring within the recess with one end abutting the shoulder, and the pull bar having shoulders for engaging the other end of the cartridge spring for urging the pull bar to a forward position in the cartridge.

7. An aortic punch for removing tissue from a vascular system comprising a handle and a punch cartridge having a pull bar with an end connector, the handle having a linear translator for linear movement along an axis, a rotary drum, a rotary translator assembled within the rotary drum with both the drum and translator having keyhole openings through their front faces for passing the pull bar end connector, the rotary translator fitted at one end to the linear translator and at its other end having a cage for receiving and retaining the end connector, the cartridge comprising a tubular housing having a longitudinal axis and having an open punch end and an open handle end, a blade drum positioned in the punch end of the housing, the blade drum having a closed cutting edge, the drum having an axial bore for slidably receiving a punch mandrel, the punch mandrel comprising a shaft with a circumferential recess for positioning vascular tissue in the aortic punch, the circumferential recess defining a punch head at an end of the shaft, the punch head having a closed cutting edge for cooperation with the drum cutting edge in removing vascular tissue, the punch mandrel having an integral pull bar having a handle end, the pull bar extending along said axis for receiving linear reciprocating motion of fixed excursion from the handle and transmitting that motion to the punch mandrel, the pull bar extending through the handle end of the tubular housing, the housing having an interior shoulder, the pull bar having a shoulder, a spring engaging the interior shoulder and the pull bar shoulder for urging the bar and mandrel to a forward position, the pull bar having the end connector for engagement with the handle so that reciprocating motion is imparted to the punch mandrel for removing vascular tissue at the blade drum, and the handle and cartridge being readily detachable to facilitate use in a surgical procedure of a single handle with a cartridge selected from a variety of cartridge sizes and configurations.

* * * * *